(12) United States Patent
Sato et al.

(10) Patent No.: US 7,444,687 B2
(45) Date of Patent: Nov. 4, 2008

(54) HEARING PROTECTIVE DEVICE THAT INCLUDES CELLULAR EARMUFFS

(75) Inventors: Luciana M. Sato, Campinas (BR); Glaucia C. Gabas, Campinas (BR); Dean M. Remer, Woodbury, MN (US); Thomas I. Insley, Lake Elmo, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 102 days.

(21) Appl. No.: 11/215,588

(22) Filed: Aug. 29, 2005

(65) Prior Publication Data

US 2007/0044205 A1    Mar. 1, 2007

(51) Int. Cl.
*A42B 1/06* (2006.01)
(52) U.S. Cl. .......................... 2/209; 128/857
(58) Field of Classification Search ............. 2/209, 2/423; 181/129; 381/379, 374, 370–372, 381/388; 128/857, 864, 865, 370–372, 388
See application file for complete search history.

(56) References Cited

U.S. PATENT DOCUMENTS

| 360,985 | A | | 4/1887 | Basch |
|---|---|---|---|---|
| 817,457 | A | | 4/1906 | Turner |
| 2,782,423 | A | | 2/1957 | Simon et al. |
| 3,190,973 | A | * | 6/1965 | Aileo .......................... 381/372 |
| 3,272,926 | A | * | 9/1966 | Falkenberg .................. 381/372 |
| 3,513,482 | A | * | 5/1970 | Holden ........................... 2/421 |
| 3,593,341 | A | * | 7/1971 | Aileo .............................. 2/209 |
| 3,795,014 | A | | 3/1974 | Simpson et al. |
| 4,104,743 | A | | 8/1978 | Bøttger |
| 4,327,065 | A | | 4/1982 | Von Dardel et al. |
| 4,471,496 | A | * | 9/1984 | Gardner et al. ................. 2/209 |
| 4,674,134 | A | | 6/1987 | Lundin |
| 4,748,694 | A | | 6/1988 | Aileo |
| 4,809,811 | A | * | 3/1989 | Gorike ........................ 181/129 |
| 4,856,118 | A | * | 8/1989 | Sapiejewski ................... 2/209 |
| 4,954,327 | A | | 9/1990 | Blount |
| 5,023,955 | A | * | 6/1991 | Murphy et al. ................. 2/209 |
| 5,509,146 | A | | 4/1996 | Bryerton, Sr. |
| 5,546,610 | A | | 8/1996 | Herzig et al. |
| 5,551,089 | A | | 9/1996 | Whidden |
| 5,551,090 | A | * | 9/1996 | Thompson ..................... 2/209 |
| 5,688,860 | A | | 11/1997 | Croft |

(Continued)

FOREIGN PATENT DOCUMENTS

EP    1404146 A1    3/2004

(Continued)

OTHER PUBLICATIONS

PCT International Search Report, International Application No. PCT/US2006/031150.

(Continued)

*Primary Examiner*—Katherine Moran
(74) *Attorney, Agent, or Firm*—Karl G. Hanson (57) ABSTRACT

A hearing protective device that includes a headpiece, a first earmuff affixed to the headband, and a second earmuff affixed to the headband, each earmuff including an ear cup that includes a cellular material and that has a distal exterior surface that includes exposed cellular material, and a proximal exterior surface.

16 Claims, 5 Drawing Sheets

U.S. PATENT DOCUMENTS

| | | | |
|---|---|---|---|
| 5,708,724 A | 1/1998 | Burris et al. | |
| 5,799,658 A * | 9/1998 | Falco | 128/864 |
| 5,813,180 A | 9/1998 | Whitney et al. | |
| 5,841,081 A | 11/1998 | Thompson et al. | |
| D403,128 S | 12/1998 | Scanlon et al. | |
| 5,913,309 A * | 6/1999 | Sheehan et al. | 128/846 |
| 5,970,160 A | 10/1999 | Nilsson et al. | |
| 5,974,757 A | 11/1999 | Whitney et al. | |
| 5,979,451 A | 11/1999 | Leight | |
| 5,996,123 A * | 12/1999 | Leight et al. | 2/209 |
| 6,148,446 A | 11/2000 | Leight | |
| D445,240 S | 7/2001 | Persson | |
| 6,289,522 B1 * | 9/2001 | Jones et al. | 2/425 |
| 6,353,938 B1 | 3/2002 | Young | |
| 6,412,593 B1 * | 7/2002 | Jones | 181/129 |
| D463,857 S | 10/2002 | Dix et al. | |
| D473,539 S | 4/2003 | O'Leary | |
| 6,557,186 B1 * | 5/2003 | Purnell | 2/425 |
| 6,598,358 B1 | 7/2003 | Schwertfeger et al. | |
| 6,611,963 B2 | 9/2003 | Woo et al. | |
| D494,711 S | 8/2004 | LeBow | |
| 7,076,077 B2 | 7/2006 | Atsumi et al. | |
| 2003/0079275 A1 | 5/2003 | Woo et al. | |
| 2004/0070222 A1 * | 4/2004 | Wong | 294/31.2 |
| 2005/0126845 A1 * | 6/2005 | Vaudrey et al. | 181/129 |
| 2005/0283882 A1 * | 12/2005 | Berger et al. | 2/209 |

FOREIGN PATENT DOCUMENTS

| | | | |
|---|---|---|---|
| FR | 2343472 A1 | | 10/1977 |
| GB | 1 229 086 | | 4/1971 |
| GB | 1229086 | * | 4/1971 |
| WO | WO 94/17763 | | 8/1994 |
| WO | WO 96/23462 | | 8/1996 |
| WO | WO 97/48296 | | 12/1997 |
| WO | WO 98/06362 | | 2/1998 |
| WO | WO 01/60293 A1 | | 8/2001 |
| WO | WO 2005/072668 A1 | | 8/2005 |

OTHER PUBLICATIONS

U.S. Appl. No. 11,215,611 to Sato et al. filed Aug. 29, 2005 entitled *Hearing Protective Earmuff Device Having Frictionally Engageable Ear Cups*.

European Standard EN 13819-2, *Hearing Protectors—Testing Part 2: Acoustic Test Methods; English version of DIN EN 13819-2*, pp. 1-11 (Nov. 2002).

Lerner, Eric J., *Less is More with Aerogels; A Laboratory Curiosity Develops Practical Uses*, The Industrial Physicist, Oct./Nov. 2004, vol. 10, Issue 5, pp. 26, 27, 29, and 32 (American Institute of Physics).

PCT International Search Report from International Application No. PCT/US2006/032420.

Abstract for FR 2,343,472.

* cited by examiner

HEARING PROTECTIVE DEVICE THAT INCLUDES CELLULAR EARMUFFS

BACKGROUND

The invention relates to cellular earmuffs.

Hearing protective devices in the form of earmuffs are widely used in industry to protect workers against environmental noise. Traditional hearing protective earmuffs include a pair of cup-shaped rigid shells that are attached to a resilient, rigid headband. The rigid outer shell of the earmuff is often made of plastic, metal or a combination thereof, and is filled with an open cell foam. The rigid outer shell generally contributes a noticeable amount of weight to the earmuff, making the hearing protective device heavier and uncomfortable to wear over time.

A cushion resides on the head-contacting portion of the earmuff and is designed to create a seal and decrease the pressure exerted by the device on the user. The cushion is annular and defines a central opening in which the ear of the user resides. Because the cushion contacts the user when the device is worn, moisture, oils, and dirt present on the user can be transferred to the cushion. To facilitate cleaning and to protect against degradation of the foam, the cushion often includes a covering in the form of a plastic film. The plastic film is often applied in a separate processing step.

In many hearing protective earmuffs, the earmuff is permanently attached to the headband and is not designed to be removable from the headband. For these constructions, attempts to remove the earmuff from the headband can damage or destroy the utility of the hearing protective device.

Traditional hearing protective earmuffs are also constructed from a number of parts that add to product complexity and overall weight. Many manufacturing steps and expensive processes are typically involved in the manufacture of these traditional hearing protective earmuffs.

SUMMARY OF THE INVENTION

In one aspect, the invention features a hearing protective device that includes a headpiece (e.g., a headband or a helmet) that includes a first earmuff affixed to the headpiece. The first earmuff includes a first ear cup that has a cellular material, a distal exterior surface that includes an exposed cellular material, and a proximal exterior surface. A second earmuff is also affixed to the headpiece and it includes a second ear cup that has a cellular material, a distal exterior surface, and a proximal exterior surface. Like the first ear cup, the second includes a distal exterior surface that includes an exposed cellular material.

The invention features a hearing protective device that includes exposed foam earmuffs that can be easily attached to and removed from the headband. The invention also features foam earmuffs that are lightweight and can be constructed from fewer components relative to existing hearing protective earmuffs having rigid plastic outer shells. The foam earmuff can be a unitary member, which can reduce manufacturing costs. In some constructions, the ear cup and cushion of the earmuff can be formed in a single step. The hearing protective earmuffs also can be easier to assemble and manufacture relative to traditional hearing protective earmuffs.

The hearing protective earmuffs can be manufactured to be free of rigid parts that can break and that render the earmuff less comfortable to wear. Because there is no need for a rigid outer plastic cover (e.g., a shell), the earmuff may transmit less noise to the user when the outside of the earmuff is contacted (e.g., hit or bumped with an object), i.e., less noise may be transmitted to the user's ears relative to an earmuff that has a hard outer plastic cover.

The foam earmuff also can be manufactured from a variety of colored foams, which can serve functional (e.g., identification, ownership, degree of sound attenuation) as well as aesthetic purposes.

Other features and advantages of the invention will be apparent from the following description of the drawings, preferred embodiments, and from the claims.

Glossary

In reference to the invention, these terms have the meanings set forth below:

The phrase "exposed cellular material," means that the surface of the cellular material is available for contact (e.g., by a user) and includes a configuration in which an integral film is present on the surface of the cellular material.

The phrase, "hearing protective device," refers to a device that provides an average (mean) real-ear-attenuation of at least 3 decibels at each of 1000 Hz, 2000 Hz, 4000 Hz, and 8000 Hz when tested according to section 4.2 of EN 13819-2: 2002.

The term "headband" means a device that is constructed to retain an earmuff and compress an earmuff against the head of a user.

The term "ear cup" means a component that is dimensioned to receive an ear of a user and is constructed to provide sound attenuation.

BRIEF DESCRIPTION OF THE DRAWINGS

Like reference symbols in the various figures of the drawing indicate like elements. The elements in the drawings are not to scale.

DETAILED DESCRIPTION OF PREFERRED EMBODIMENTS

A hearing protective device 10 that includes a headpiece in the form of a headband 12, and two earmuffs 14a, 14b affixed to the headband 12 at the ends 32 of the headband 12 is illustrated in FIGS. 1-6 and 12. The headband 12 resiliently holds the earmuffs 14a, 14b against a user's ears. The earmuffs 14a, 14b include an ear cup 16 and an annular cushion 18 attached to the ear cup 16.

Figure 4:
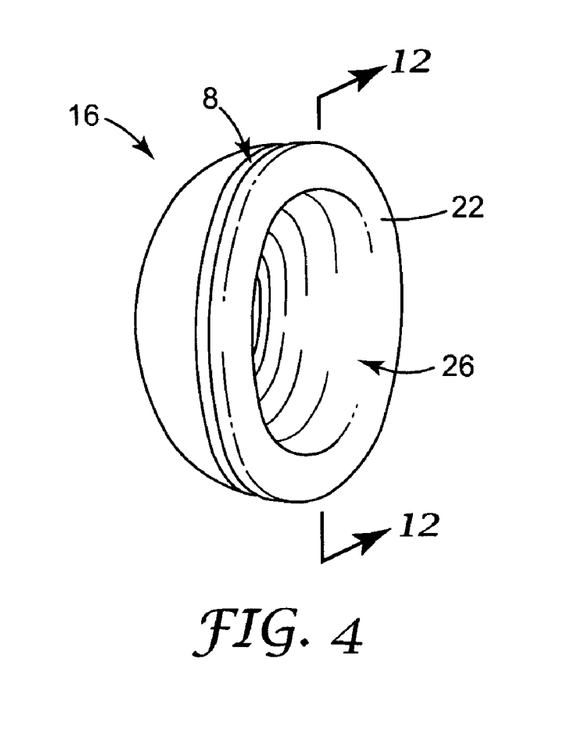
FIG. 4 is a perspective view of the ear cup of FIG. 1.
Figure 12:
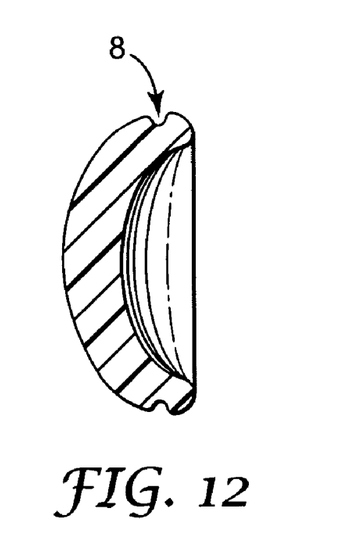
FIG. 12 is a view taken in cross section along line 12-12 of FIG. 4.

The ear cup 16 is made of a gas filled cellular material, absorbs sound and attenuates noise, e.g., inhibits and preferably prevents sound waves, from reaching the ear canal of the user. The ear cup 16 is generally cup-shaped such that the distal 20 exterior surface is generally arcuate in shape and the proximal 22 exterior surface, i.e., the surface closest to the ear, is generally concave and provides an open region 26 in which the ear of a user can reside. The distal exterior surface 20 of the ear cup 16 is exposed to the environment such that it can be contacted by a user. The ear cup 16 is free of an exterior rigid shell such as a plastic or metal shell. The ear cup 16 includes a channel 8 for receiving an end 32 of the headband 12.

The ear cup 16 includes any suitable gas filled cellular material that attenuates sound. Useful sound attenuating materials include gas filled cellular materials that exhibit acoustic attenuation, mechanical stiffness and formability (e.g., exhibiting the property of being able to alter the material, e.g., by cutting, shaping, molding, or a combination thereof). Examples of useful gas filled cellular materials including, e.g., foams (e.g., closed cell foams, open cell foams, slow recovery resilient foams (e.g., pressure molded slow recovery resilient foams), instantaneous recovery foams), bonded fiber structures, aerogels, acoustic composite materials including, e.g., hollow ceramic particles in a matrix of synthetic resin binder, multiple layered acoustic composite materials, and combinations thereof. Examples of suitable cellular bonded fiber structures are described in U.S. Pat. No. 5,841,081 and incorporated herein. Examples of aerogels are described in U.S. Pat. Nos. 4,954,327 and 6,598,358 and incorporated herein. Examples of suitable acoustic composite materials are described in U.S. Pat. Nos. 5,813,180 and 5,688,860 and incorporated herein. The cellular material preferably is an open cell foam. The foam can be a hard foam, a semi-rigid foam, or a flexible foam.

The cells of the foam preferably have a relatively larger average cross-sectional area at the interior of the foam, and a relatively smaller average cross-sectional at the exterior surface of the foam. The presence of smaller cells at the exterior surface of the ear cup provides a more rigid, stiff exterior layer relative to the interior foam. In some embodiments, the compacted smaller cells at or near the exterior surface of the ear cup form an integral skin on the ear cup, e.g., a film layer that results from the molding process, at the surfaces of the ear cup. The integral skin essentially includes closed cells and can include some open cells to allow the release of gas, e.g., air. Altering various parameters of the manufacturing process can alter the thickness of the integral skin. The mold temperature, for example, can influence the presence and nature of the integral skin. In some foam molding process a relatively thinner skin is formed with increasing temperatures, whereas a thicker, relatively denser skin forms at lower temperatures. One example of a useful mold temperature range for forming an integral skin is from about 35° C. to about 70° C. The integral skin can have any desired thickness. One example of a useful range of skin thickness is from about 1 mm to about 5 mm.

Useful compositions from which the foam can be formed include, e.g., polyurethanes, polyvinyl chloride, and combinations thereof. Suitable hard polyurethane foams can be from polyols having a molecular weight less than 800. Suitable semi-rigid polyurethane foams can be formed from polyols having a molecular weight from about 800 to 2000, and suitable flexible polyurethane foams can be formed from polyols having a molecular weight greater than 2000. Useful polyurethane foams have any desired density including, e.g., a density ranging from about 200 kg/m$^3$ to about 1100 kg/m$^3$, or even from about 200 kg/m$^3$ to about 800 kg/m$^3$. Suitable foams and methods of making the same are also described, e.g., in U.S. Pat. No. 5,979,451 and incorporated herein.

The cellular material can optionally include a coloring agent, e.g., dye, pigment and combinations thereof. The coloring agent can provide identification, a desired aesthetic property, a visible indication of the sound attenuation properties the ear cup, and combinations thereof. The ear cups can also optionally include other indicia of the level of sound attenuation provided thereby including, e.g., markings, colorings, and combination thereof.

Alternatively or in addition the ear cups can include markings in various forms including, e.g., logos, colors, designs, imprints, relief, and combination thereof.

Figure 5:
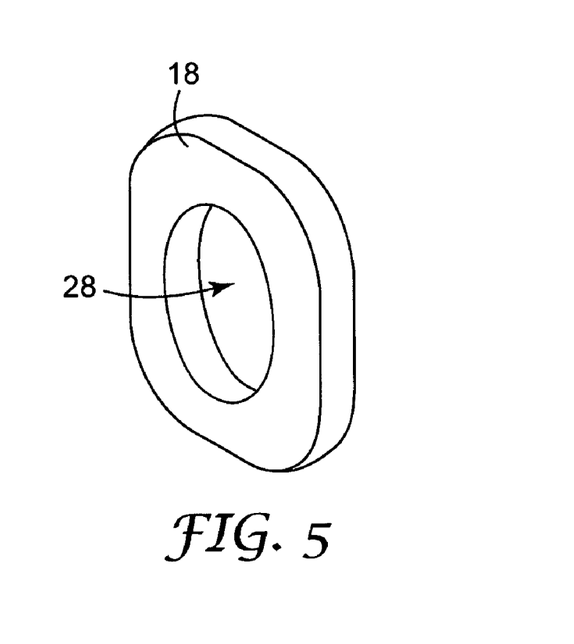
FIG. 5 is a perspective view of the cushion of the earmuff of FIG. 2.

The cushion 18 seals the earmuff 14 around the ear of the user and dampens the pressure exerted by the hearing protective device 10 against the user's head. The annular cushion 18 defines an aperture 28, which accommodates the ear of a user. The cushion 18 is generally rectangular in shape with four concave corner segments and four connecting segments defining the aperture 28. Alternatively, the cushion 18 can be of any suitable shape including, e.g., oval, round, square and rectangular, and can define an aperture having any suitable shape including, e.g., oval, round, square and rectangular.

The cushion includes any suitable cellular material. Useful cellular materials include the materials set forth above including, e.g., closed cell foams, open cell foams, and combinations thereof, and can exhibit a variety of properties including, e.g., viscoelasticity, high resiliency, and combinations thereof. Preferably the cushion is a foam cushion. Preferably the foam of the cushion is not as stiff as the foam of the ear cup 16. Useful foam compositions include, e.g., polyurethanes, polyvinyl chloride, and combinations thereof. Preferably the cushion exhibits instantaneous recovery.

The cushion 18 can optionally include an integral skin as described above with respect to the foam ear cup.

Alternatively or in addition, the cushion 18 can include a covering, e.g., a cover, a layer, a film, a coating, and combinations thereof. A covering can protect the integrity of the form, inhibit soiling of the foam, and enhance the cleaning properties of the cushion. The covering can also provide aesthetic appeal to the cushion including, e.g., texture, color, and combinations thereof. The covering can be continuous or discontinuous. Preferably the covering is present on the cellular material such that air is allowed to release from the cellular material. To facilitate release of air, the covering can include micro holes (e.g., puncture holes) or cracks of a size sufficient to allow release of air from the cellular material. Alternatively the covering can include a single hole of a size sufficient to allow the release of air to conform the cushion to the surface of the user with which it is in contact. The covering can be in the in the form of a film (e.g., a self-supporting film), woven (e.g., fabric) or nonwoven web, and comprised of any suitable composition including, e.g., synthetic polymer, natural polymer, and combinations thereof.

The cushion 18 can be affixed to the proximal exterior surface 22 of the ear cup 16 through any suitable mechanism including, e.g., mechanical devices, adhesive compositions, and combinations thereof. In one embodiment, the foam of cushion 18 and the foam of ear cup 16 are at least partially unreacted such that the polymerization reaction is completed after the two parts are contacted with each other. The in situ polymerization causes the two parts to bond to each other. In another embodiment, the foam of one of the parts (i.e., the first part) is completely reacted (e.g., polymerized) and the other part (i.e., the second part) is formed (e.g., foamed) on top of the first part, through which process the first part is affixed to the second part. In other embodiment, the cushion 18 and ear cup 16 bond to each other when contacted with each other while still tacky. Alternatively or in addition, the foams are completely reacted and the cushion is affixed to the ear cup using a suitable mechanism including, e.g., an adhesive composition, mechanical mechanisms (e.g., male-female connections, and frictional engagements), and combinations thereof.

Figure 1:
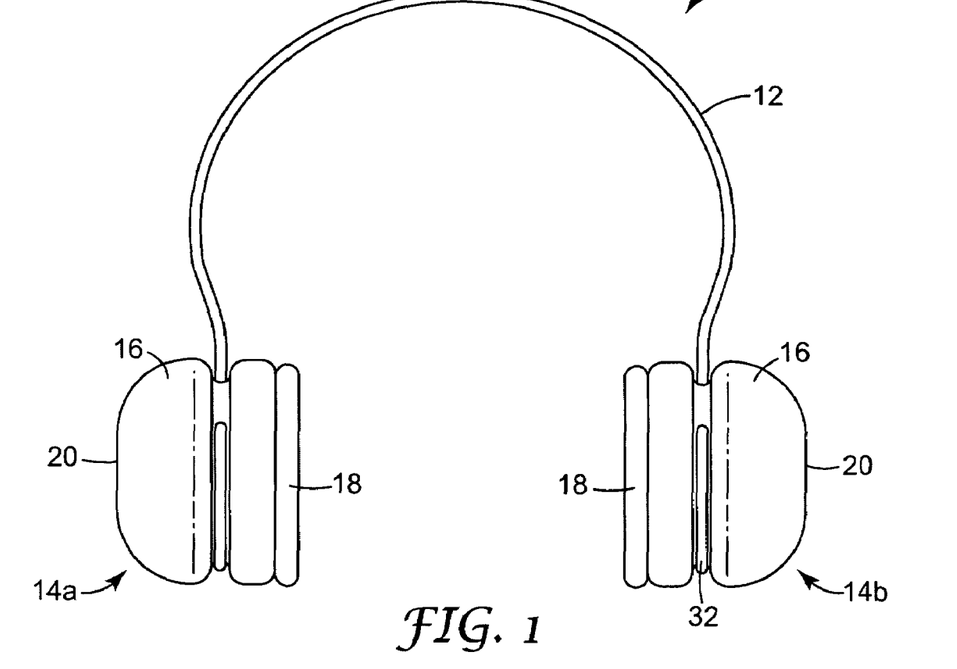
FIG. 1 is a plan view of a hearing protective device.
Figure 2:
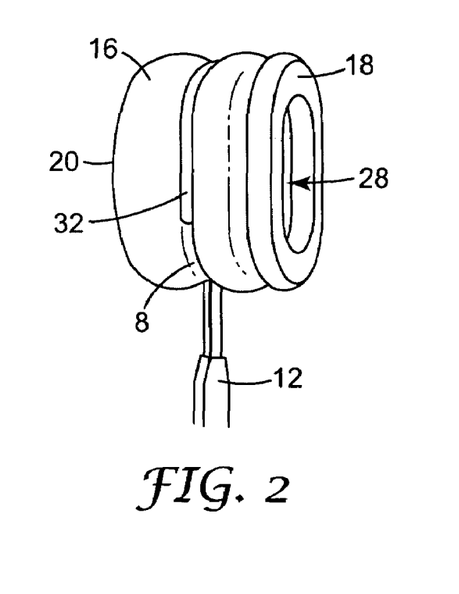
FIG. 2 is a perspective view of an earmuff attached to a portion of the headband of the hearing protective device of FIG. 1.
Figure 3:
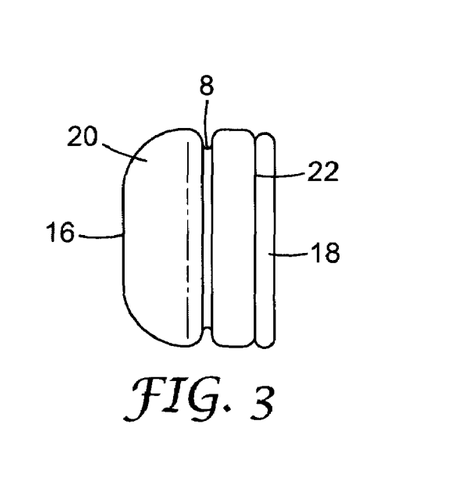
FIG. 3 is a side view of the earmuff of the hearing protective device of FIG. 1.
Figure 6:
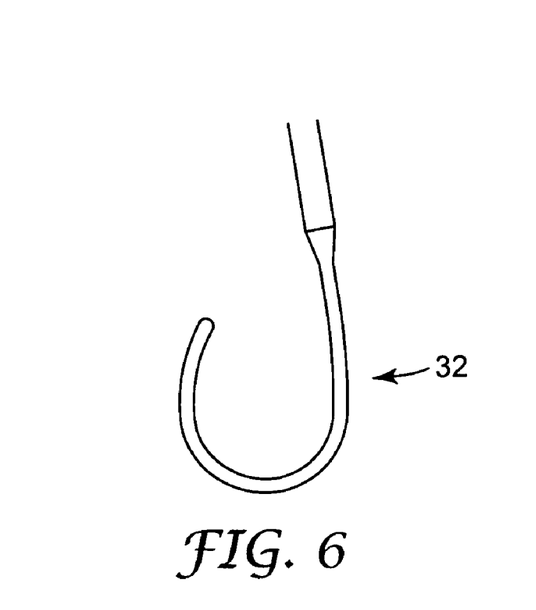
FIG. 6 is a side view of an end portion of the headband of FIG. 1.

The headband 12 is generally U-shaped and sufficiently resilient to allow the open end of the U to be splayed apart to fit the device to the head of the user. When the device 10 is in place on the user's head the recovery forces generated in the strained headband 12 bias the earmuffs 14a, 14b inwardly against the user's head and foster secure attachment and good acoustic sealing of the earmuffs 14a, 14b to the user's head. The terminal ends 32 of the U-shaped headband 12 are in the shape of a hook for releasably retaining the earmuffs 14a, 14b such that a user can remove the earmuffs 14a, 14b (e.g., used earmuffs) from the headband 12, affix earmuffs 14a, 14b (e.g., new earmuffs) to the headband 12, and combinations thereof as desired. The hook 32 slides around the ear cup 16 and retains the ear cup 16 in position until removed by the user.

The headband 12 can be adjustable in length. Mechanisms for making resilient headbands adjustable in length are well known in the art and include, e.g., a pair of overlapping sliding members with mechanisms for maintaining the members in alignment and mechanisms for securing the overlapped portions at the desired length, a pair of telescoping nested members having mechanisms to secure the nested portions together at the desired length, and a central headband of fixed length that includes a mechanism, e.g., cooperative rack-and-pinion, toothed, interrupted thread or a combination thereof, whereby each end of the headband can be separately adjusted relative to the central headband and secured at the adjusted length. One example of a useful adjustable headband is present in product number 1440 from 3M Company (St. Paul, Minn.).

The headband can be configured to be capable of assuming a variety of positions including, e.g., being positioned over the head, behind the user's neck, under the user's chin, and combinations thereof. In some embodiments, the headband position can be altered by constructing the headband and ear cup such that the headband can rotate about the ear cup from a first position to a second position.

Useful headband materials include, e.g., plastic, and metal, e.g., spring steel, copper-beryllium alloys, composites, and combinations thereof. Useful plastic materials include, e.g., thermoplastic polymers (e.g., polypropylene, polyethylene, polyamide, e.g., nylon, polyester, and combinations thereof), thermoplastic elastomers, thermoset polymers, and combinations thereof. Useful composites include a polymer matrix and a filler including, e.g., fibers, particulate, and combinations thereof.

Figure 7:
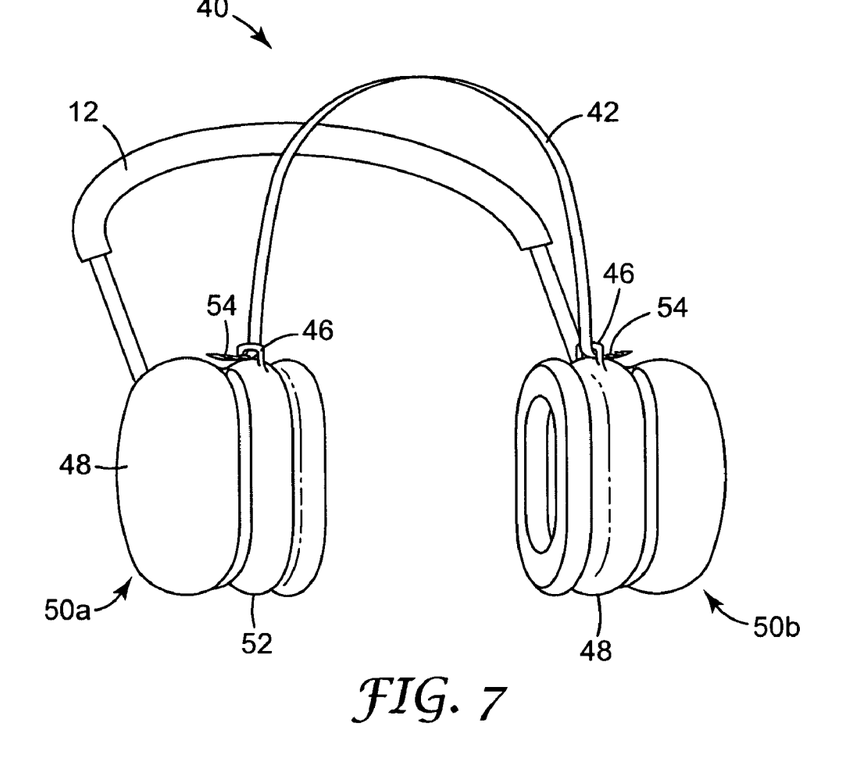
FIG. 7 is a plan view of a hearing protective device according to another embodiment.
Figure 8:
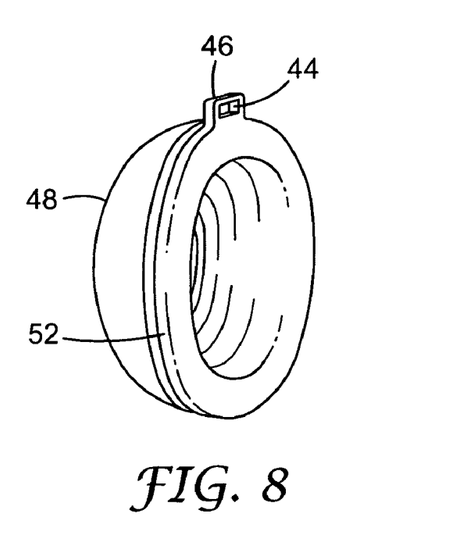
FIG. 8 is a perspective view of an ear cup of FIG. 7.

Other embodiments are within the claims. The hearing protective device can also include a strap in addition to the headband. Preferably the length of the strap is adjustable, e.g., through a friction fit, such that the strap assists in maintaining the earmuff in position on the user. The strap can help maintain the earmuff in position on the user, e.g., when the headband is positioned behind the user's head, e.g., near the neck of the user. When the headband is positioned behind the neck, the strap can be positioned over the head to help maintain the earmuffs in position over the ears. Preferably the strap is relatively thin so that the user can wear a head covering (e.g., a hard hat) over the strap while simultaneously wearing the earmuff. FIGS. 7 and 8 illustrate an embodiment of the hearing protective device 40 that includes a headband 12, a strap 42, a first earmuff 50a, and a second earmuff 50b. A loop 46 extends from a rigid plastic ring 52 that encircles the ear cup 48. Each end of the strap 42 passes through an aperture 44 defined by the loop 46 on each of the ear cups 48. Ridges 54 extend from the strap 42 near the ends of the straps 42 to prevent the ends from sliding back through the aperture 44. The strap 42 remains fixed in place and can be adjusted by forcibly moving a ridge 54 through the aperture 44 in the appropriate direction. Any suitable material can be used for the strap including, e.g., elastic, film (e.g., plastic, i.e., polymer, films), and combinations thereof. Although, element 52 is described as a separate component in the form of a rigid plastic ring, element 52 including loop 46 can be simultaneously formed in the mold used to form the earmuff or ear cup and can be made from the same material as the earmuff or ear cup.

Figure 9:
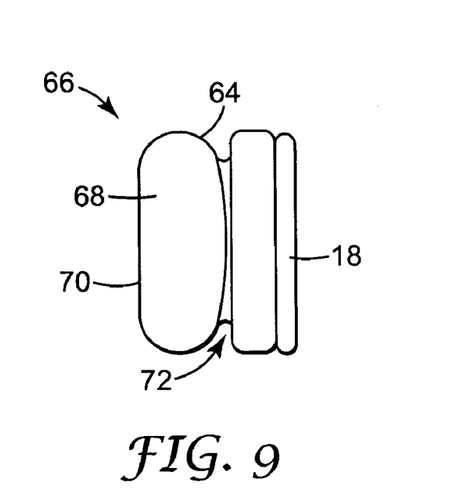
FIG. 9 is a side view of another embodiment of an earmuff.

FIG. 9 illustrates an embodiment of an earmuff 66 in which a portion of one side wall 64 of the channel 72 of the ear cup 68 extends away from the center of the channel 72 toward the distal exterior surface 70 of the ear cup 68 to provide greater freedom of movement to the ear cup 68 as it is held in position on a user by a headband (not shown). The cutaway portion 64 from the side wall allows the cup 66 to pivot thereby providing greater range of motion (e.g., movement) to the cup. In other embodiments, the bottom wall of the channel defines a circle, which allows a circular hook to rotate around the channel of the earmuff, which in turn allows the headband to rotate from various positions including, e.g., a first position (e.g., a position over the head), to a second position (e.g., a position behind the neck).

Figure 10:
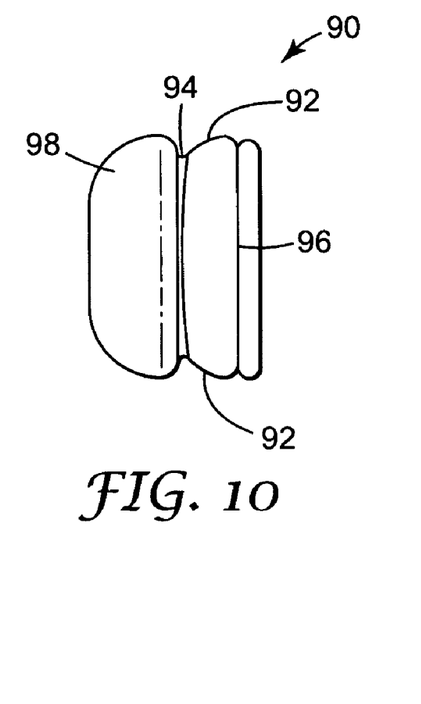
FIG. 10 is a side view of an earmuff according to another embodiment.

FIG. 10 illustrates an embodiment of an earmuff 90 in which a portion of the side wall 92 of the channel 94 extends away from the center of the channel 94 toward the proximal surface 96 of the ear cup 98.

Figure 11:
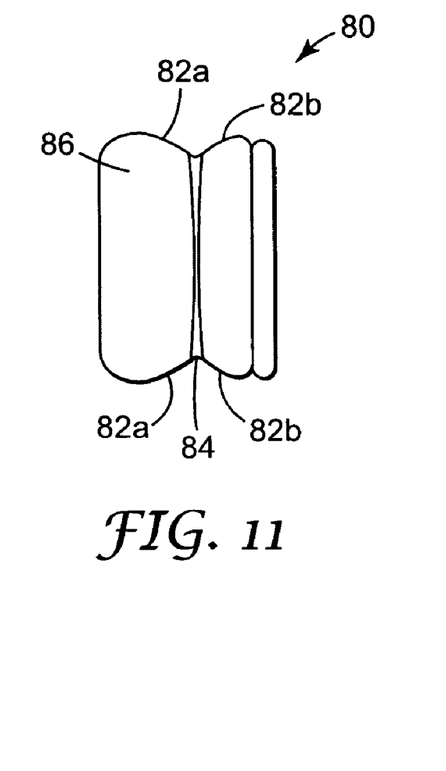
FIG. 11 is a side view of an earmuff according to another embodiment.

FIG. 11 illustrates an embodiment of an earmuff 80 in which a portion of both side walls 82a, 82b of the channel 84 of the ear cup 86 extend away from the center of the channel 84.

Figure 13:
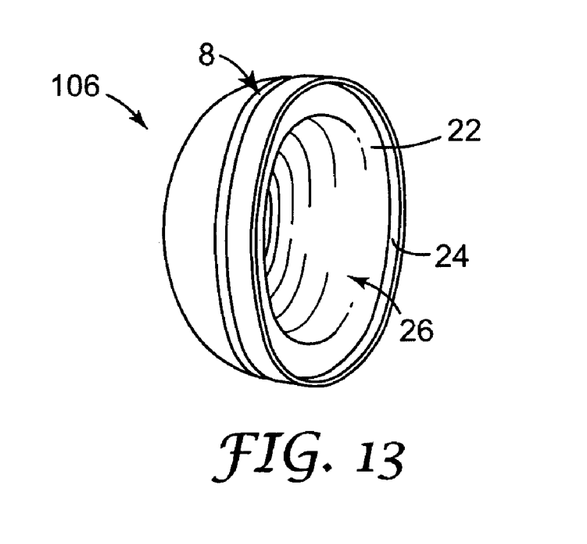
FIG. 13 is a perspective view of an ear cup according to another embodiment.

FIG. 13 illustrates an embodiment of the ear cup 106 in which a flange 24 extends away from the proximal exterior surface 22 of the ear cup 16. In use, a cushion 18 (not shown) affixed to the ear cup 106 sits against a portion of the proximal exterior surface 22 and is releasably retained in position on the ear cup 106 through a friction fit with the flange 24.

Although the cushion and ear cup have been described as separate components, the ear cup and cushion can be formed (e.g., molded) as a single unit. Alternatively, the cushion can be formed in place on the proximal surface of the ear cup.

In some embodiments, the earmuff includes a communication component, e.g., an ear phone or speaker. The communication component can be molded in situ during the formation of the foam of the ear cup or inserted into the ear cup after formation of the ear cup.

Figure 14:
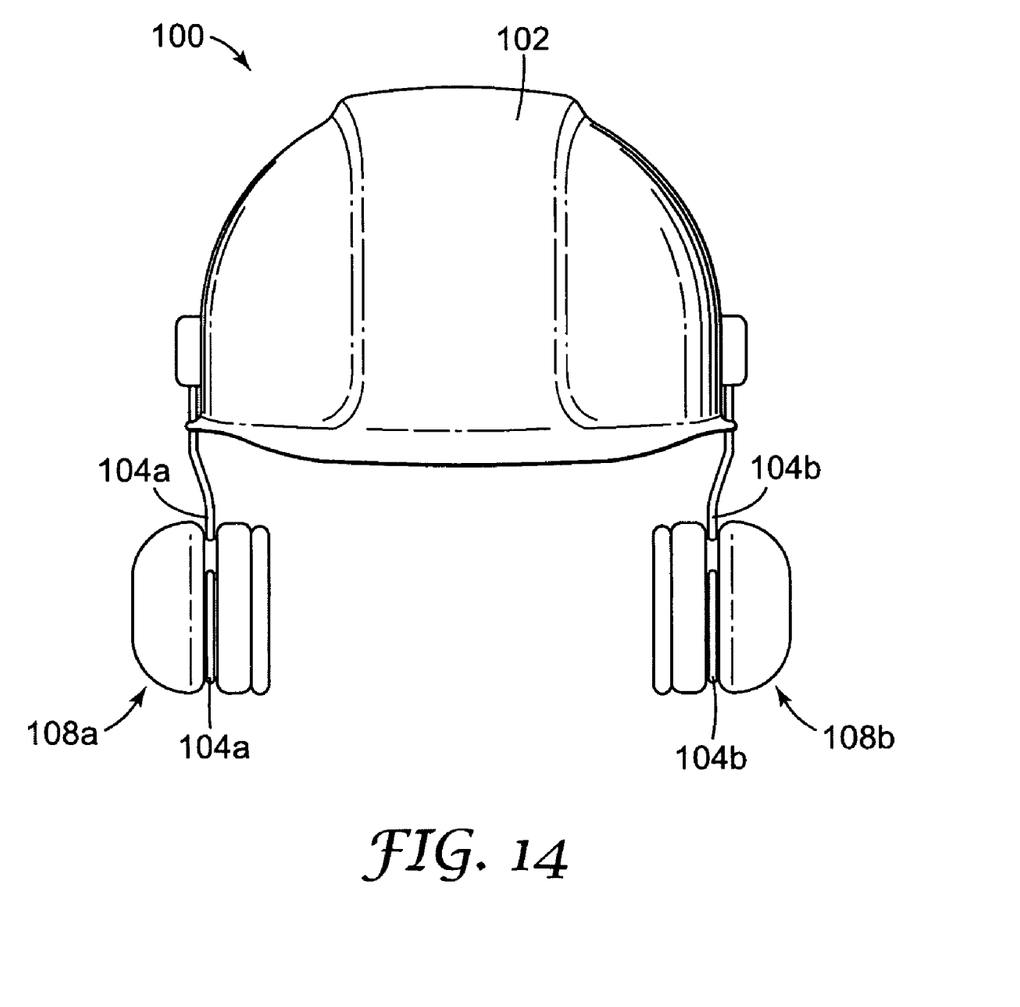
FIG. 14 illustrates another embodiment of the hearing protective device.

FIG. 14 illustrates another embodiment of the hearing protective device 100 in which the headpiece 102 is a head covering in the form of a helmet. The ends 104a, 104b of the headpiece are affixed to the exterior surface of the helmet 102 and extend from the helmet 102 to the ear of a user. Earmuffs 108a, 108b are positioned in an opening in the ends 104a, 104b and the ends 104a, 104b bias the earmuffs 108a, 108b inwardly against the user's head. The ends are moveable between a first position in which they are biased against the user's head and a second position in which they are held away from the user's head. Examples of mechanisms that attach an extension to a helmet and permit movement of the extension from a first position to a second position can be found in U.S. Pat. No. 5,546,610 and incorporated herein.

Although the foam earmuffs have been described as being releasably retained in the ends of the head band, the earmuffs can be permanently retained by the head band. The earmuffs also can be attached to the headband through any suitable mechanism including, e.g., mechanical devices, adhesives and combinations thereof.

All patents and patent applications cited above including those in the Background section are incorporated into this patent application in total.

The invention may take on various modifications and alterations without departing from its spirit and scope. Accordingly, this invention is not limited to the above-described but is to be controlled by the limitations set forth in the following claims and any equivalents thereof.

This invention also may be suitably practiced in the absence of any element not specifically disclosed herein.

What is claimed is:

1. A hearing protective device that comprises:
   a headpiece;
   a first earmuff affixed to the headpiece and comprising a first ear cup, and a second earmuff also affixed to the headpiece and comprising a second ear cup;
   the first and second ear cups each further comprising a cellular material and having
      a distal exterior surface comprising exposed cellular material and
      a proximal exterior surface;
   wherein the cellular material comprises foam having an exterior portion and an interior portion, the interior portion of the foam comprises cells having a relatively larger average cross-sectional area, and the exterior surface of the foam comprises cells having a relatively smaller average cross-sectional area.

2. The hearing protective device of claim 1, further comprising
   a first cushion affixed to the proximal exterior surface of the first ear cup; and
   a second cushion affixed to the proximal exterior surface of the second ear cup.

3. The device of claim 2, wherein the first and second cushions comprise polyurethane foam.

4. The device of claim 2, wherein the first and second cushions are bonded to the first and second ear cups, respectively, through an adhesive composition.

5. The device of claim 2, wherein each of the first and second ear cups comprises foam of a first density and the affixed cushion comprises foam of a second density, the first density being greater than the second density.

6. The device of claim 1, wherein the first and second ear cups each comprise polyurethane foam.

7. The device of claim 2, wherein the first and second cushions and the first and second ear cups of the respective first and second earmuffs comprise foam, wherein the foam of the first and second ear cups is stiffer than the foam of the first and second cushions.

8. The device of claim 1, wherein the ear cup and cushion of each of the first and second earmuffs are a single unitary structure.

9. The device of claim 1, wherein the headpiece comprises two ends,
   the first end being at least partially positioned in a first channel of the first ear cup; and
   the second end being at least partially positioned in a second channel of the second ear cup.

10. The device of claim 1, wherein the exterior surface of the first and second ear cups comprises an integral skin.

11. The device of claim 1, wherein a majority of the cells of the foam at the exterior surface of the first and second ear cups are closed.

12. The device of claim 1, wherein the headpiece comprises a headband.

13. The device of claim 1, wherein the headpiece comprises a helmet.

14. The device of claim 1, wherein the first and second earmuffs each comprise indicia representing the level of sound attenuation provided thereby.

15. The device of claim 14, wherein the indicia comprises a coloring agent.

16. The device of claim 1, wherein the channel is annular.

* * * * *